United States Patent
Kirchhofer et al.

(10) Patent No.: US 6,613,023 B2
(45) Date of Patent: Sep. 2, 2003

(54) DEVICE FOR ADMINISTERING AN INJECTABLE PRODUCT IN DOSES

(75) Inventors: Fritz Kirchhofer, Sumiswald (CH); Thomas Gurtner, Koppigen (CH)

(73) Assignee: Disetronic Licensing AG, Burgdor (CH)

( * ) Notice: Subject to any disclaimer, the term of this patent is extended or adjusted under 35 U.S.C. 154(b) by 131 days.

(21) Appl. No.: 09/903,297

(22) Filed: Jul. 11, 2001

(65) Prior Publication Data

US 2001/0051792 A1 Dec. 13, 2001

(51) Int. Cl.[7] ................................................ A61M 5/00
(52) U.S. Cl. ...................... 604/208; 604/209; 604/211
(58) Field of Search .................................. 604/131, 134, 604/135, 187, 207, 208, 209, 210, 211, 218, 224

(56) References Cited

U.S. PATENT DOCUMENTS

| | | | |
|---|---|---|---|
| 2,695,023 A | 11/1954 | Brown | 128/218 |
| 3,605,744 A | 9/1971 | Dwyer | 128/218 F |
| 4,082,121 A | 4/1978 | Sturm et al. | 141/27 |
| 4,313,439 A | 2/1982 | Babb et al. | 128/214 F |
| 4,552,561 A | 11/1985 | Eckenhoff et al. | 604/869 |
| 4,592,745 A | 6/1986 | Rex et al. | 604/211 |
| 4,659,327 A | 4/1987 | Bennett et al. | 604/135 |
| 4,735,611 A | 4/1988 | Anderson et al. | 604/130 |
| 4,813,870 A | 3/1989 | Pitzen et al. | 433/90 |
| 4,865,591 A | 9/1989 | Sams | 604/186 |
| 4,883,472 A | 11/1989 | Michel | 604/208 |
| 4,894,054 A | 1/1990 | Miskinyar | 604/136 |
| 4,936,833 A | 6/1990 | Sams | 604/232 |
| 4,946,446 A | 8/1990 | Vadher | 604/198 |

(List continued on next page.)

FOREIGN PATENT DOCUMENTS

| | | | |
|---|---|---|---|
| CA | 2 155 575 | 7/1999 | .......... A61M/5/315 |
| DE | 2 056 688 | 3/1972 | ............ A61M/5/28 |
| DE | 19519147 A1 | 12/1995 | ............ A61M/5/20 |
| EP | 0 265 214 | 4/1988 | .......... A61K/37/26 |
| EP | 0 279 583 A2 | 8/1988 | ............ A61M/5/34 |
| EP | 0 295 075 A1 | 12/1988 | .......... A61M/5/315 |
| EP | 0 498 737 A1 | 8/1992 | .......... A61M/5/315 |
| JP | 4-256757 | 9/1992 | .......... A61M/5/315 |
| JP | 4-256758 | 9/1992 | .......... A61M/5/315 |
| JP | 5-161713 | 6/1993 | .......... A61M/5/315 |
| WO | WO 91/10460 | 7/1991 | ............ A61M/5/24 |
| WO | WO 93/16740 | 9/1993 | |
| WO | WO 94/17846 | 8/1994 | .......... A61M/5/315 |
| WO | WO 94/26331 | 11/1994 | ............ A61M/5/20 |
| WO | WO 96/07443 | 3/1996 | .......... A61M/5/315 |
| WO | WO 97/30742 | 8/1997 | .......... A61M/5/178 |
| WO | WO 00/41753 | 7/2000 | .......... A61M/5/315 |

OTHER PUBLICATIONS

Cutler, Paul, "Deferoxamine Therapy in High–Ferritin Diabetes", Journal of American Diabetes Associateion, vol. 38, No. 10, (5pgs) (Oct. 1989).

Primary Examiner—Manuel Mendez
Assistant Examiner—Mark K. Han
(74) Attorney, Agent, or Firm—Dorsey & Whitney LLP

(57) ABSTRACT

The invention concerns a device for administering an injectable product in doses, wherein the device includes a casing, comprising a reservoir for the product, a piston, which when moved in a feed direction towards an outlet of the reservoir forces product from the reservoir, a gear rack, moving the piston in the feed direction, comprising a first series of teeth and a second series of teeth, a drive member, movable relative to the casing in and counter to the feed direction, and slaving the gear rack when moved in the feed direction, and a blocking means, arranged secured against shifting relative to the casing and cooperating with one of the series of teeth such that it prevents the gear rack from being moved counter to the feed direction and allows the gear rack to be moved in the feed direction.

11 Claims, 2 Drawing Sheets

U.S. PATENT DOCUMENTS

| | | | |
|---|---|---|---|
| 4,973,318 A | 11/1990 | Holm et al. | 604/208 |
| 5,015,235 A | 5/1991 | Crossman | 604/117 |
| 5,017,190 A | 5/1991 | Simon et al. | 604/207 |
| 5,059,181 A | 10/1991 | Agran | 604/110 |
| 5,114,406 A | 5/1992 | Gabriel et al. | 604/136 |
| 5,244,465 A | 9/1993 | Michel | 604/208 |
| 5,273,544 A | 12/1993 | van der Wal | 604/134 |
| 5,279,585 A | 1/1994 | Balkwill | 604/207 |
| 5,279,586 A | 1/1994 | Balkwill | 604/207 |
| 5,304,152 A | 4/1994 | Sams | 604/207 |
| 5,337,756 A | 8/1994 | Barbier et al. | 128/763 |
| 5,480,387 A | 1/1996 | Gabriel et al. | 604/134 |
| 5,496,293 A | 3/1996 | Huggenberger | 604/208 |
| 5,514,097 A | 5/1996 | Knauer | 604/136 |
| 5,549,558 A | 8/1996 | Martin | 604/110 |
| 5,584,815 A | 12/1996 | Pawelka et al. | 604/191 |
| 5,599,323 A | 2/1997 | Bonnichsen et al. | 604/272 |
| 5,611,783 A | 3/1997 | Mikkelsen | 604/208 |
| 5,626,566 A | 5/1997 | Petersen et al. | 604/208 |
| 5,634,903 A | 6/1997 | Kurose et al. | 604/110 |
| 5,643,214 A | 7/1997 | Marshall et al. | 604/134 |
| 5,679,111 A | 10/1997 | Hjertman et al. | 604/135 |
| 5,807,346 A | 9/1998 | Frezza | 604/208 |
| 5,984,900 A | 11/1999 | Mikkelsen | 604/208 |
| 6,042,571 A | 3/2000 | Hjertman et al. | 604/208 |
| 6,086,567 A | 7/2000 | Kirchhofer et al. | 604/211 |
| 6,228,067 B1 * | 5/2001 | Gabriel | 604/211 |
| 6,241,709 B1 * | 6/2001 | Bechtold et al. | 604/207 |

* cited by examiner

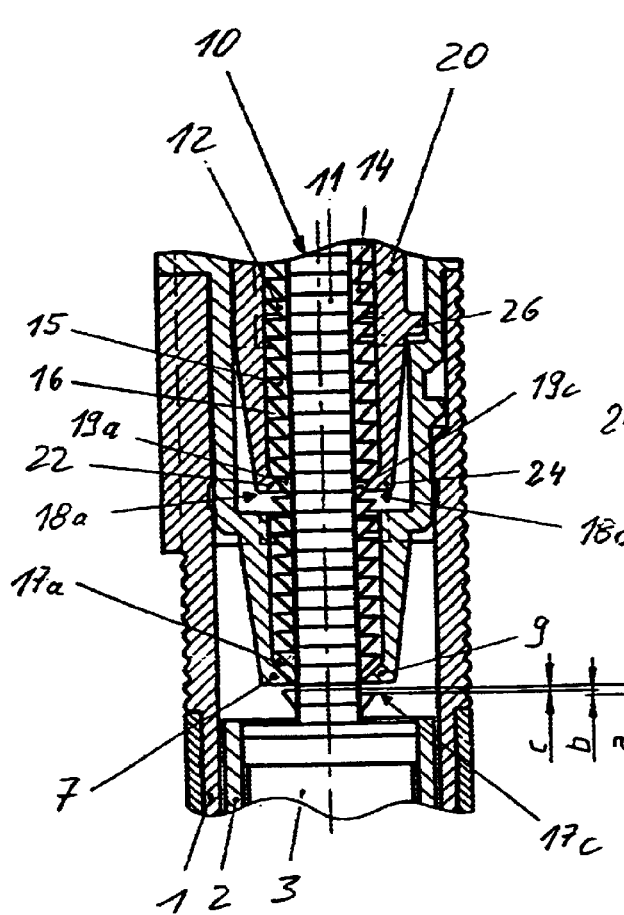
Fig. 3
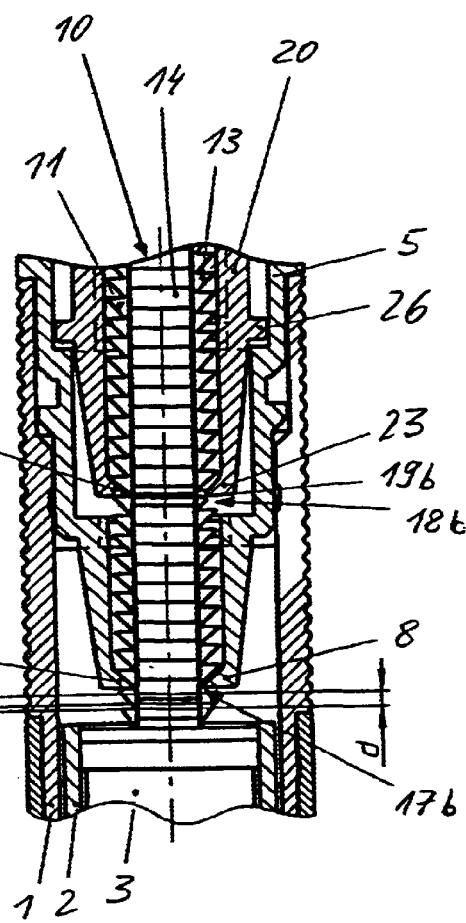
Fig. 2
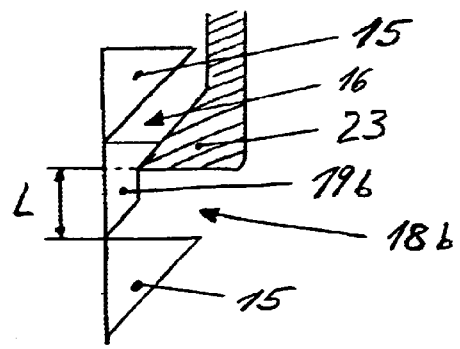

DEVICE FOR ADMINISTERING AN INJECTABLE PRODUCT IN DOSES

BACKGROUND OF THE INVENTION

1. Technical Field

The invention relates to a device for administering an injectable product in doses.

2. Description of the Related Art

A device such as the invention relates to is known, for example, from WO 97/36626. This device comprises a casing, comprising a reservoir for the product. Accommodated in the reservoir is a piston which, when moved in a feed direction towards an outlet of the reservoir, forces product out of the reservoir. A gear rack, which pushes against the piston, moves the piston in the feed direction. The gear rack is provided with series of teeth. In the casing, a drive member is furthermore accommodated, movable in and counter to the feed direction relative to the casing, said drive member slaving the gear rack when moved in the feed direction. For this purpose, the drive member meshes with the series of teeth in the gear rack via slaving means. When moved, only one of the slaving means is ever pushing against the back of a tooth of a series of teeth. For setting the amount of product administered by one piston stroke, the drive member in a front position is manually retracted counter to the feed direction by a set dosage path length, the slaving means of the drive member thereby sliding over the series of teeth and giving elastically. The gear rack is prevented from being moved backwards by blocking means accommodated secured against shifting relative to the casing. The blocking means cooperate with one of the series of teeth of the gear rack, such that the blocking means prevent the gear rack from being moved counter to the feed direction and allow the gear rack to be moved in the feed direction by giving elastically. When the gear rack is moved, the blocking means do not fully mesh with the tooth gaps of the series of teeth simultaneously. Only one of the blocking means is ever meshed with a tooth gap, while another is elastically bent away, pushing against the flank of a tooth.

The alternating mesh during movement in the feed direction, advantageous with respect to accuracy and safety during dosing and administering, loses this advantage after a lengthy storage period, which from factory to initial use usually amounts to several months, or does not even take effect, due to material fatigue in a blocking or slaving means bent away during storage.

SUMMARY OF THE INVENTION

It is an object of the invention to assure, with great certainty, precise dosing and administering of the product, even after a lengthy storage period, in such a device for administering an injectable product in doses.

The object is solved by the subject of the independent claims.

A device for administering an injectable product in doses comprises a casing, comprising: a reservoir for the product; a piston, which when moved in a feed direction towards an outlet of the reservoir forces product out of the reservoir; a gear rack, moving the piston in the feed direction, comprising a first series of teeth and a second series of teeth; a drive member, movable relative to the casing in and counter to the feed direction, and slaving the gear rack when moved in the feed direction; and a blocking means, arranged secured against shifting relative to the casing and cooperating with one of the series of teeth, such that it prevents the gear rack from being moved counter to the feed direction and allows the gear rack to be moved in the feed direction.

Preferably, at least two blocking means are provided, which do not fully mesh with the tooth gaps of the series of teeth simultaneously. Only one of the blocking means is ever meshed with a tooth gap, while the other is elastically pushed away, pushing against the flank of a tooth perpendicular to the feed direction.

In accordance with the invention, at least one of the at least two series of teeth of the gear rack comprises an elongated tooth gap, with which the blocking means cooperating with said series of teeth meshes, when the gear rack assumes a starting position prior to a first administering. The drive member and the gear rack assume the starting position relative to each other after assembly and up until a first administering. Thus, in the starting position, each of at least two blocking means meshes with a tooth gap. By maintaining the alternating mesh, advantageous for administering, material fatigue in the blocking means is prevented.

Preferably, at least two slaving means are connected secured against shifting to the drive member, each of them cooperating with one of the series of teeth, such that only one of the at least two slaving means is pushed in the feed direction against a tooth of the gear rack when the drive member is moved in the feed direction, while the other elastically gives on the flank of a tooth. By giving elastically, the slaving means allow the drive member to be moved counter to the feed direction and relative to the gear rack.

In accordance with the invention, at least one of the at least two series of teeth of the gear rack comprises an elongated tooth gap, with which the slaving means cooperating with this series of teeth meshes when the gear rack assumes the cited starting position prior to a first administering. In this way, material fatigue in the slaving means is prevented.

An elongated tooth gap is understood as a tooth gap which, when viewed in the feed direction, is longer than the other, regularly provided tooth gaps in the series of teeth, which will be termed regular tooth gaps in the following. A blocking or slaving means is able to mesh with the elongated region in a longer region than in regular tooth gaps, preferably with the same depth of mesh as when the blocking means meshes with a regular tooth gap in the blocking position or as when the slaving means meshes with a regular tooth gap in the abutting position. The mesh is in any event fuller than would be the case if a regular tooth gap opposed the blocking or slaving means in the starting position. A mesh is accordingly termed full mesh when a blocking or slaving means protrudes right into the root of an interdental space, or when a blocking or slaving means protrudes towards the gear rack to the same extent as in a blocking or abutting position.

It is particularly preferred in the starting position that both an elongated tooth gap for at least one of the at least two blocking means as well as an elongated tooth gap for at least one of the at least two slaving means are provided in the at least two series of teeth. The elongated tooth gap for the blocking means and the elongated tooth gap for the slaving means may be provided in a single series of teeth. It is, however, also possible for the one elongated tooth gap to be provided in one series of teeth and the other elongated tooth gap in the other series of teeth.

The series of teeth of the gear rack are preferably serrated, comprising teeth which taper in the feed direction. The blocking and slaving means is/are preferably adapted in shape, such that pushing away is hindered as little as possible by friction when the gear rack is moved in the feed direction, and movement counter to the feed direction is securely blocked by a purely positive mesh. In principle, however, the series of teeth may also show a different shape, as long as the two requirements of allowing movement in the feed direction and securely preventing movement counter to the feed direction are fulfilled.

The series of teeth are preferably provided opposite or also adjacent to each other on the gear rack; in principle, however, they could be provided in any region of the gear rack with a corresponding height offset in the blocking and/or slaving means. The slaving means, however, are preferably arranged level with each other, and the alternating mesh achieved by offsetting the series of teeth by a fraction of a pitch. The blocking means are likewise preferably arranged level with each other.

The slaving means and the blocking means work in the same way to fulfill their respective functions, by abutting against the back of a tooth of the gear rack and so slaving or blocking the gear rack, and allowing the gear rack to be retracted or advanced, by giving elastically. They may be provided identically or differently. Elastic give is preferably achieved by bending a tongue extending in the direction of movement, perpendicular to the direction of movement of the gear rack. In principle, it would also be possible, for example, for a cam to be mounted, perpendicularly movable against the elastic restoring forces.

In one embodiment variant, the gear rack is equipped with a third series of teeth with which a third blocking means meshes, wherein the third blocking means also does not mesh with a tooth gap of the gear rack simultaneously with the at least two other blocking means. Preferably, a fourth series of teeth is also provided at the same height on the gear rack, with which a fourth blocking means meshes. In accordance with the invention, the third series of teeth—and in the case of a fourth series of teeth, the fourth series of teeth—also comprises an elongated tooth gap with which the respective blocking means meshes in the starting position of the gear rack.

In a preferred example embodiment, including a third series of teeth, the drive member preferably comprises a third slaving means. The third slaving means of the drive member also does not mesh with a tooth gap of the gear rack simultaneously with the at least two other slaving means of the drive member, such that it pushes against a tooth of the gear rack when moved in the feed direction. The three slaving means mesh alternately. If a fourth series of teeth is provided, the drive member preferably comprises a fourth slaving means.

Thus, a particularly finely adjusted alternating mesh of the blocking and/or slaving means is possible, while still preventing material fatigue due to lengthy storage.

In one embodiment variant, the at least two blocking means mesh with the at least two series of teeth of the gear rack, while two slaving means of the drive member mesh with two other series of teeth of the gear rack. Through the resulting alternating arrangement of the slaving means and blocking means around the gear rack, it is possible to shorten the length of the gear rack and thus the length of the device. The blocking and slaving means may be provided at the same height with respect to the feed direction. An alternating mesh of the blocking means among each other and of the slaving means among each other is nonetheless possible. The Applicant reserves the right to seek separate patent protection for the device with and without the form of an elongated tooth base.

BRIEF DESCRIPTION OF THE DRAWINGS

Preferred example embodiments of the invention will now be detained in the following, with reference to the Figures, in which:

FIGS. 2 and 3 show the gear rack in detail, comprising blocking and slaving means in mesh.

DETAILED DESCRIPTION

Figure 1:
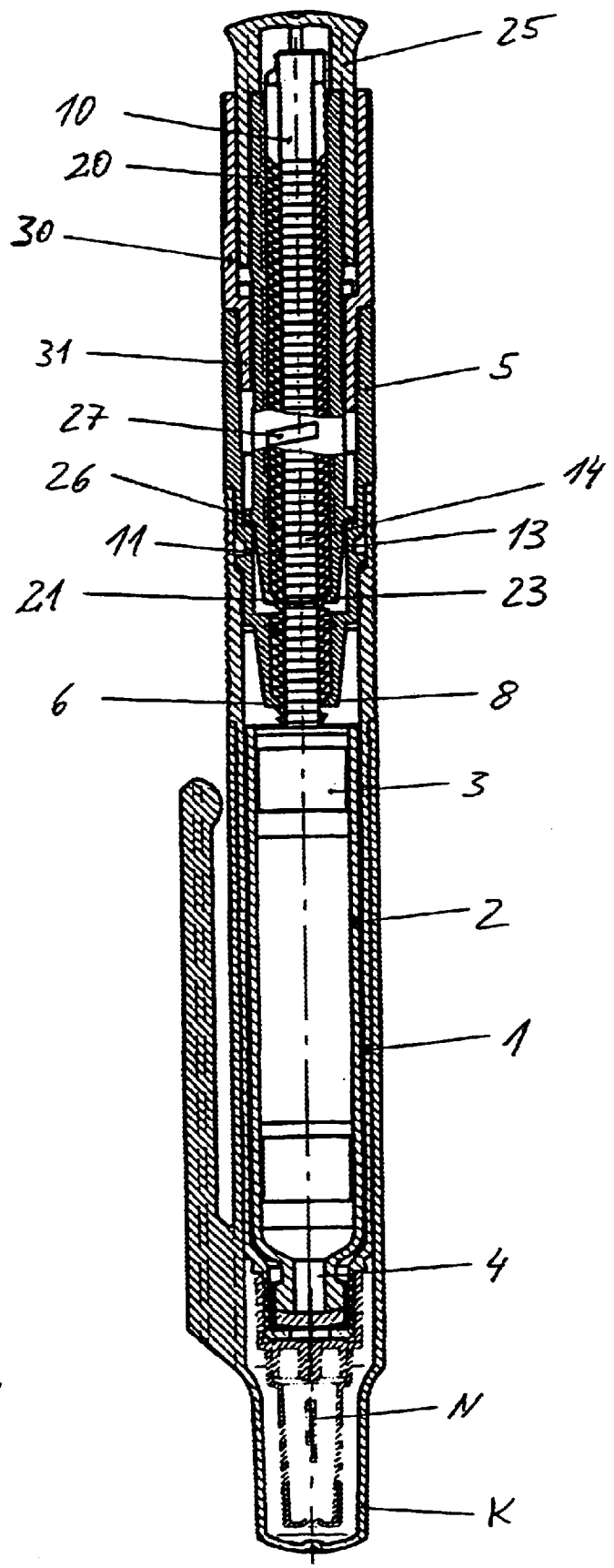
FIG. 1 show an injection device, comprising a gear rack with four series of teeth.

FIG. 1 is a longitudinal sectional view of an injection device, in the example embodiment an injection pen. FIGS. 2 and 3 show a detail thereof in two longitudinal sectional views, perpendicular to each other.

The injection device comprises a casing, comprising a front casing sleeve 1, and a rear casing sleeve 5 firmly connected thereto. The front casing sleeve 1 serves to accommodate an ampoule 2. Contained in the ampoule 2 is a liquid product in the form of an active substance, for example insulin. A piston 3 is further accommodated in the ampoule 2. Moving the piston 3 in the feed direction towards an ampoule outlet 4 forces the product out of the ampoule 2 through its outlet 4 and delivers it through an injection needle N. The front casing sleeve 1 is protected by a cap K. The needle N is further protected by a needle cap.

The piston 3 is moved in the feed direction by a drive means accommodated in the rear casing sleeve 5. The drive means comprises a drive member 20, and a gear rack 10 acting directly on the piston 3 as a driven member. The drive member 20 is mounted in the rear casing sleeve 5, linearly movable in and counter to the feed direction of the piston 3. A lid 25, connected secured against shifting to the drive member 20, protrudes out of the rear of the casing.

A dosing member 30, provided as a sleeve body, is connected secured against shifting to the rear casing sleeve 5, but rotatable about the common longitudinal axis. Twisting the dosing member 30 sets the maximum dosage path length which the drive member 20 and the gear rack 10 may cover in the feed direction, and so also the maximum product dosage which may be delivered in an injection. For this purpose, a front sleeve portion 31 of the dosing member 30 is provided, spirally encircling at its front area, i.e. the front sleeve portion 31 progressively falls away circumferentially from a foremost front area section, relative to the longitudinal axis of the injection device. The dosing member 30 maybe formed in accordance with, for example, a dosing member as described in WO 97/36625, and during dosage may cooperate with the drive member 20, as described therein.

Dosage takes place in the foremost position of the drive member 20 with respect to the feed direction, in which a collar or cam 26 extending radially from the outer surface area of the drive member 20 abuts a stopper formed by the rear casing sleeve 5. In this foremost position of the drive member 20, the dosing member 30 is twisted relative to the rear casing sleeve 5 until it has reached the desired dosing position. In this dosing position, a clear dosage space remains between a further collar or cam 27, likewise extending from the outer surface area of the drive member 20, and the front area of the dosing member 30 opposite said collar or cam 27. The drive member 20 can be retracted relative to the rear casing sleeve 5, and thus also relative to the piston 3, counter to the feed direction, by said dosage space. By pulling the lid 25, it is manually retracted. The dosage space equates to the dosage path length for the subsequent administering.

When the drive member 20 is retracted, the gear rack 10 remains in its sliding position relative to the casing, assumed during dosage. It is secured against moving counter to the feed direction by blocking means 6 and 8 provided on the rear casing sleeve 5. The blocking means 6 and 8 are locking cams, each provided at a front end of an elastically giving tongue, and protruding radially inwards from the tongue towards the gear rack 10. Each of the blocking means 6 and 8 cooperates with a series of teeth of the gear rack 10 facing it, such that they allow the gear rack 10 to be moved in the feed direction and prevent it from being moved counter to the feed direction by a positive mesh.

The gear rack 10 is formed by a rod of rectangular cross-section, provided with a series of serrated teeth on each of its four sides, in a front region with respect to the feed direction. In FIG. 2, two series of teeth, provided on opposite sides of the gear rack 10 and opposite the blocking means 6 and 8, are designated 11 and 13. In addition to the two series of teeth 11 and 13, the gear rack 10 comprises two further series of serrated teeth, provided on opposite side faces of the gear rack 10, one of which is designated 14 in FIG. 1. The individual teeth 15 of each of the series of teeth of the gear rack 10 are each tapered in the feed direction; in the example embodiment, the flanks of teeth are plane and oblique. The back of each tooth 15 is simply plane and points perpendicular to the feed direction and thus to the longitudinal direction of the injection device and of the gear rack 10. The regular tooth gaps in the series of teeth are respectively designated 16.

The four series of teeth show the same pitch. Within a pitch, they are arranged in an offset to each other with respect to the feed direction. The offset between series of teeth is indicated in FIGS. 2 and 3 by a, b and c.

The blocking means 6 and 8, and two further blocking means 7 and 9 cooperating with the further series of teeth 12 and 14 facing them respectively, are situated at the same height with respect to the feed direction at an angular spacing of 90° respectively. Because of the offset between the series of teeth, only one of the blocking means 6 to 9 is ever fully meshed in a tooth gap 16 of the series of teeth facing it, when the gear rack 10 is moved forwards. Each of the other three blocking means is opposed by flanks of teeth 15 of the series of teeth facing them, such that said other blocking means are bent away from the gear rack 10. When the gear rack 10 is moved in the feed direction, the blocking means 6 to 9 successively mesh fully with the series of teeth facing them in each case; overall, this results in an alternating mesh of the blocking means. Each blocking means elastically fully latching into or onto an interdental space blocks the gear rack 10 against moving counter to the feed direction.

The gear rack 10 is moved in the feed direction by the drive member 20. For this purpose, the drive member 20 tapers off in the feed direction into four tongues carrying at their front ends locking cams projecting radially inwards. Of the slaving means so formed, the two opposing slaving means 21 and 23 are illustrated in FIG. 1. In the example embodiment, the slaving means and the blocking means are alike in their form and function, both being formed on elastically giving tongues by locking cams. When the drive member 20 is moved in the feed direction, one of the slaving means pushes respectively against the back of one of the teeth 15 of the series of teeth facing it, thus slaving the gear rack 10 in the feed direction. Due to the give of the slaving means and the forward sweep of the teeth 15, the slaving means slide over the series of teeth of the gear rack 10 blocked by the blocking means, when the drive member 20 is moved counter to the feed direction. Since the slaving means taper off into locking cams level with respect to the feed direction, two of the slaving means are never fully meshed with one of the regular tooth gaps 16 of the gear rack 10 simultaneously.

In FIGS. 1 to 3, the injection device is shown in a starting position, in which the gear rack 10 assumes its rearmost position relative to the rear casing sleeve 5 and also relative to the drive member 20. In this starting position, the rear casing sleeve 5 comes from the manufacturer fully assembled with the gear rack 10 and drive member 20, including the lid 25 and the dosing member 30. The starting position thus corresponds to the storage position of the injection device, in particular for the drive means and dosing means of the injection device. In the example embodiment, the injection device is a disposable pen. Reusability, i.e. replacing the ampoule, may however be achieved with simple modifications.

In the starting position of the injection device, with the ampoule 2 inserted, the product dose to be administered in the first injection is set by the user. For this purpose, the dosing member 30 is twisted to a certain rotational position, corresponding to the desired product dose. In this rotational position, the cam 27 of the drive member 20 comprises the clear dosage space from the opposing front area of the dosing member 30. Only the blocking means 6 abuts the back of a tooth of the series of teeth 11 in the starting position. The other blocking means 7, 8 and 9 are pre-latched into their disengaged neutral positions towards the gear rack 10, but in the starting position they locate into the tooth gaps 17a, 17b and 17c, which are elongated in comparison to the regular tooth gaps 16. Of the slaving means, only the slaving means 21 abuts the back of a tooth in the starting position. In the starting position, the other slaving means 22, 23 and 24 are located disengaged in their neutral positions in the tooth gaps facing them, i.e. they are not bent away in the starting position. Each of the series of teeth 12, 13 and 14 comprises a tooth in front of its tooth gaps 17a, 17b and 17c. These teeth, which define the tooth gaps 17a, 17b and 17c in the feed direction, serve solely as a functional test of the injection device. Directly after the device has been assembled, the gear rack 10 is pushed into the starting position by the blocking means 6 to 9 arranged concentrically around it.

The drive member 20 is retracted counter to the feed direction from its foremost position with respect to the rear casing sleeve 5 by manually pulling the lid 25. As the drive member 20 is retracted, its slaving means 21 to 24 slide over the series of teeth of the gear rack 10 facing them, the blocking means 6 preventing them from being slaved.

During injection, the drive member 20 and thus also the gear rack 10 are moved by the dosage path length in the feed direction by pressing the lid 25, the gear rack 10 pushing the piston 3 in the ampoule 2 towards the outlet 4, and product being delivered. In the starting position as shown in the Figures, only the slaving means 21 abuts against the back of a tooth of the gear rack 10.

In the example embodiment, the slaving means of the drive member 20 are arranged behind the blocking means with respect to the feed direction. The concentric arrangement of the blocking means and slaving means is such that they can be bent radially outwardly away from the gear rack 10, against their own elastic restoring forces, according to the shape of the teeth of the series of teeth of the gear rack 10. In the example embodiment, each of the blocking means and each of the slaving means are located together, level with respect to the feed direction, while the series of teeth of the gear rack 10 are offset relative to each other such that the regular tooth gaps 16 in the series of teeth are located at differing heights with respect to the feed direction. This has the effect that there is never more than one blocking means or one slaving means meshed with one of the regular tooth gaps 16. Instead of this arrangement, the blocking means and the slaving means may also accordingly be arranged offset at differing heights with respect to the feed direction, and the series of teeth of the gear rack 10 arranged level. The arrangement chosen in the example embodiment, however, has advantages for production engineering.

By equipping the gear rack 10 with four series of teeth, savings in the overall length of the drive means and dosing means may be possible, while maintaining the advantages of the alternating mesh by arranging all the blocking means and slaving means level with respect to the feed direction. This may be achieved by two blocking means, for example blocking means 6 and 8, meshing with two of the four series of teeth of the gear rack 10, and at the same height, two slaving means of the drive member 20 meshing with the two other series of teeth. By pairing the blocking means and the slaving means, the advantages of the alternating mesh may yet be maintained, by correspondingly offsetting the series of teeth or the blocking and slaving means.

In the starting position as shown in the Figures, which is also the storage position, in particular for the parts of the injection device accommodated in the rear casing sleeve 5, namely the gear rack 10, the drive member 20 and the blocking means 6 to 9, the danger of material fatigue would exist for the blocking means and slaving means which cannot latch into tooth gaps 16 in the starting position, such that they are at least partly or, as in the example embodiment, completely disengaged. These blocking and slaving means would namely be bent away in the starting position. When bent away, the slaving and blocking means are elastically biased. If this condition is maintained over lengthy periods, it cannot be guaranteed with the necessary certainty that they will elastically bend back into the function position, namely the position abutting against the back of a tooth.

The gear rack 10, however, comprises elongated tooth gaps where the blocking and slaving means mesh in the starting position of the injection device, which do not abut the backs of teeth of the gear rack 10 in the starting position.

FIGS. 2 and 3 will now be discussed in combination.

The gear rack 10 is provided on each of its four sides, direct from the front area facing the piston 3, with a series of serrated teeth of the same shape and pitch. These four series of teeth are rotationally designated 11, 12, 13 and 14. The first series of teeth 11 comprises individual serrated teeth 15 in succession, in a regular pitch and without gaps. In the starting position shown in the Figures, the blocking means 6 and the slaving means 21, arranged behind it as viewed from the piston 3, each mesh with one of the regular tooth gaps 16, such that they abut the backs of teeth, as viewed in the feed direction.

Following the first series of teeth 11 in rotation around the gear rack 10 is the second series of teeth 12 shown in FIG. 3. The second series of teeth 12 is identical to the first series of teeth 11, except for the following differences.

Firstly, the teeth 15 of the second series of teeth 12 are arranged offset along the gear rack 10 with respect to the feed direction by a fraction of a pitch, namely by the length d from the teeth 15 of the first series of teeth 11. This offset, and the arrangement of the blocking means 6 and 7 at the same height, means that only one of the blocking means 6 and 7 is ever in full mesh at any one time, in which it assumes its disengaged neutral position. This applies, but with one exception, which accounts for a second difference from the first series of teeth 11, namely: an elongated tooth gap 17a with which the blocking means 7 meshes in the starting position is provided in a front region of the second series of teeth 12. The blocking means 7, which in a completely regular formation of the second series of teeth 12 would be bent away from the gear rack 10 in the starting position, is also in full mesh due to the elongation of the tooth gaps 17a beyond the regular dimensions of the second series of teeth 12. Thus, the tongue forming the blocking means 7 at the front end in the starting position is not elastically bent.

The second series of teeth 12 comprises a further difference in the form of a further elongated tooth gap 18a, behind the elongated tooth gap 17a as viewed from the piston 3. In the starting position, the second slaving means 22 of the drive member 20 comes to rest unbiased in this further elongated tooth gap 18a. The meshing sequence of the slaving means 21 and 22 corresponds to that of the blocking means 6 and 7.

Following the first series of teeth 11 via the second series of teeth 12 further in rotation around the gear rack 10 is the third series of teeth 13 shown in a longitudinal sectional view in FIG. 2. The third series of teeth 13 is provided with an elongated tooth gap 17b and a further elongated tooth gap 18b in which the third blocking means 8 and the third slaving means 23 mesh in their respective neutral positions, i.e. unbiased, corresponding to the fitting position in the starting position.

Following the third series of teeth 13 in rotation, further around the gear rack 10, is a fourth series of teeth 14. Like the second series of teeth 12 and the third series of teeth 13, this comprises an elongated tooth gap 17c and a further elongated tooth gap 18c with which the fourth blocking means 9 and the fourth slaving means 24 fully mesh in the starting position, and therefore without biasing the tongues carrying them.

The elongated tooth gaps 17a, 17b and 17c are arranged at the same height in accordance with the arrangement of the blocking means 7, 8 and 9 meshing with them in the starting position. The same applies to the further elongated tooth gaps 18a, 18b, 18c, likewise provided on the gear rack 10 at the same height with respect to the feed direction.

The elongated tooth gaps 17a and 18a are formed differently.

The elongated tooth gap 17a is formed by leaving out one tooth when casting the gear rack 10 or by subsequently removing a whole tooth 15.

The further elongated tooth gap 18a is formed by removing only part or casting only part of a tooth, such that the second slaving means 22 meshing with the elongated tooth gap 18a is located nearer to the nearest back of a tooth of the second series of teeth 12 counter to the feed direction than the first slaving means 21 is to the nearest back of a tooth of the first series of teeth 11 counter to the feed direction. The back of the tooth in the second series of teeth 12 closing the elongated tooth gap 18a is nearer to the piston 3 than the back of the tooth in the first series of teeth 11 closing the meshing tooth gap 16 in the starting position. Thus, when the drive member 20 leaves the starting position for the first dosage, the second slaving means 22 abuts against the back of a tooth in front of the first slaving means 21.

The third series of teeth 13 is illustrated in the region of its elongated tooth gap 18b in detail beneath FIG. 2. The elongated tooth gap 18b is formed by the middle tooth of three teeth in sequence not projecting as far from the gear rack as the two regular teeth 15 adjacent to it. The middle tooth is truncated and designated 19b. It is formed in such a way that the slaving means 23 is located against a flank of the tooth 19b in the starting position, with at most a slight bias, and preferably no bias. In this way, the back of a tooth remains in the elongated tooth gap 18b on the tooth 19b formed in this way, at a height of the gear rack 10 at which the back of a tooth would similarly be located if all the teeth of the series of teeth 13 were formed completely regularly. The slaving means 23 is able to fully mesh with this elongated tooth gap 18b over a length L. The other elongated tooth gaps 18a and 18c for the slaving means 22 and 24 are formed similarly to the elongated tooth gap 18b, although their lengths L are shorter than that of the elongated tooth gap 18b.

The blocking means 6 to 9 do not project as far into the tooth gaps 16 as the slaving means 21 to 24, once they are fully latched onto the gear rack 10.

The elongated tooth gaps 18a, 18b and 18c could equally be formed by simply omitting a tooth, i.e. they may be formed like the elongated tooth gaps for the blocking means. The elongated tooth gaps 17a, 17b and 17c could be formed by retaining a truncated tooth, preferably in the manner of the elongated tooth gaps 18a, 18b and 18c. It would be just as possible to swap the configuration. The form of the elongated tooth gap shown in the example embodiment, for the slaving means on the one hand and the blocking means on the other, is however the preferred form.

In the starting position, the first blocking means 6 blocks the gear rack 10 from being moved counter to the feed direction. In this starting position, the product dosage to be administered with the next injection is first selected using the dosing member 30 shown in FIG. 1. Then, the drive member 20 is retracted by the dosage space corresponding to said dosage, the slaving means 21 to 24 thereby sliding over the teeth 15 of the series of teeth facing them in each case, the offset of the series of teeth ensuring that the slaving means 21 to 24 successively latch in regular alternation, as a result of which a number of locking procedures occur within a pitch for each single slaving means. In the rearmost position of the drive member 20 determined by the dosing member 30, it may be guaranteed with far greater certainty that at least one of the slaving means 21 to 24 will latch than would be the case with only one series of teeth and one slaving means. This also correspondingly applies to the cooperation between the series of teeth and the blocking means 6 to 9. When the drive member 20 is moved counter to the feed direction, and also when the gear rack 10 is moved in the feed direction, one each of the slaving means and the blocking means fully meshes in turn, and thus in slaving mesh and blocking mesh respectively, each latching into an elongated tooth gap in the starting position. Directly following the starting position, this is the slaving means 23, cooperating with the third series of teeth 13. Due to the simple form of the tooth gaps 17a, 17b and 17c, the blocking means 6 is the first of the blocking means to undergo blocking mesh, when the gear rack 10 is moved for a first administering.

In the foregoing description a preferred embodiment of the invention has been presented for the purpose of illustration and description. It is not intended to be exhaustive or to limit the invention to the precise form disclosed. Obvious modifications or variations are possible in light of the above teachings. The embodiment was chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A device for administering an injectable product in doses, comprising:
    a) a casing comprising a reservoir for said product;
    b) a piston which when moved in a feed direction towards an outlet of said reservoir forces product out of said reservoir;
    c) a gear rack moving said piston in said feed direction, comprising a first series of teeth and a second series of teeth;
    d) a drive member movable relative to said casing in and counter to said feed direction, and slaving said gear rack when moved in said feed direction; and
    e) at least two blocking means arranged secured against shifting relative to said casing each co-operating with one of said series of teeth such that said blocking means prevent said gear rack from being moved counter to said feed direction and allow said gear rack to be moved in said feed direction by giving elastically, wherein said blocking means do not fully mesh with the tooth gaps of said series of teeth simultaneously, when said gear rack is moved; wherein
    f) said second series of teeth comprises an elongated tooth gap with which said blocking means co-operating with said second series of teeth meshes, when said gear rack assumes a starting position prior to a first administering.

2. The device as set forth in claim 1, characterized in that a tooth gap arranged in said series of teeth directly behind said elongated tooth gap as viewed from said piston is the next tooth gap of said at least two series of teeth with which one of said at least two blocking means meshes.

3. The device as set forth in claim 1, characterized in that said gear rack comprises a third series of teeth with which a third blocking means meshes, and in that said third blocking means also does not fully mesh with a tooth gap of said gear rack simultaneously with said at least two other blocking means, when said gear rack is moved.

4. The device as set forth in claim 3, characterized in that said third series of teeth also comprises an elongated tooth gap with which said third blocking means cooperating with said third series of teeth fully meshes, when said gear rack assumes a starting position prior to a first administering.

5. The device as set forth in claim 3, characterized in that said gear rack comprises a fourth series of teeth with which a fourth blocking means meshes, and in that said fourth blocking means also does not fully mesh with a tooth gap of said gear rack simultaneously with said at least two other blocking means, and preferably also not simultaneously with said third blocking means, when said gear rack is moved.

6. The device as set forth in claim 5, characterized in that said fourth series of teeth also comprises an elongated tooth gap with which said fourth blocking means cooperating with said fourth series of teeth fully meshes, when said gear rack assumes a starting position prior to a first administering.

7. A device for administering an injectable product in doses comprising:
    a) a casing comprising a reservoir for said product;

b) a piston which when moved in a feed direction towards an outlet of said reservoir forces product out of said reservoir;

c) a gear rack moving said piston in said feed direction, comprising a first series of teeth and a second series of teeth;

d) a drive member movable relative to said casing in and counter to said feed direction, to which at least two slaving means are connected secured against shifting, each of which co-operates with one of said series of teeth such that only one of said at least two slaving means pushes in said feed direction against a tooth of said gear rack when said drive member is moved, while on the flank of a tooth the other gives elastically, wherein said slaving means allow said drive member to move counter to said feed direction and relative to said gear rack by giving elastically; and e) a blocking means arranged secured against shifting relative to said casing and co-operating with one of said series of teeth such that it prevents said gear rack from being moved counter to said feed direction and allows said gear rack to be moved in said feed direction; wherein f) said second series of teeth comprises an elongated tooth gap with which said slaving means co-operating with said second series of teeth meshes, when said gear rack assumes a starting position prior to a first administering.

8. The device as set forth in claim 7, characterized in that a tooth gap arranged directly behind said elongated tooth gap in said second series of teeth as viewed from said piston is the next tooth gap of said at least two series of teeth with which one of said at least two slaving means meshes.

9. The device as set forth in claim 7, characterized in that said gear rack is provided with a third series of teeth with which a third slaving means of said drive member meshes, such that only one of said slaving means pushes in said feed direction against a tooth of said gear rack, when said drive member is moved, and said slaving means allow said drive member to move counter to said feed direction and relative to said gear rack by giving elastically, and in that said gear rack in said third series of teeth comprises an elongated tooth gap with which said slaving means cooperating with said third series of teeth meshes, when said gear rack assumes said starting position.

10. The device as set forth in the claim 9, characterized in that said gear rack is provided with a fourth series of teeth with which a fourth slaving means of said drive member meshes, such that only one of said slaving means is pushed in said feed direction against a tooth of said gear rack, when said drive member is moved, and said slaving means allow said drive member to be moved counter to said feed direction and relative to said gear rack by giving elastically, and in said gear rack in said fourth series of teeth comprises an elongated tooth gap with said slaving means cooperating with said fourth series of teeth meshes, when said gear rack assumes a starting position.

11. A device for administering an injectable product in doses, comprising:

a casing comprising a reservoir for said product, said reservoir comprising an outlet;

a piston which, when moved in a feed direction towards the outlet, forces product out of said reservoir;

a gear rack for moving said piston in said feed direction, comprising a first series of teeth and a second series of teeth;

a drive member movable relative to said casing in and counter to said feed direction, and slaving said gear rack when moved in said feed direction; and blocking means secured against shifting relative to said casing and co-operating with said series of teeth such that said blocking means prevents said gear rack from being moved counter to said feed direction and allows said gear rack to be moved in said feed direction by giving elastically, wherein said blocking means do not fully mesh with said series of teeth simultaneously when said gear rack is moved; wherein said second series of teeth comprises an elongated tooth gap with which said blocking means meshes when said gear rack assumes a starting position prior to a first adminstering.

* * * * *